(12) United States Patent
Rajasekharan

(10) Patent No.: US 9,618,495 B2
(45) Date of Patent: Apr. 11, 2017

(54) CARBON QUANTIFYING APPARATUS AND METHOD

(75) Inventor: Vishnu Rajasekharan, Fort Collins, CO (US)

(73) Assignee: Hach Company, Loveland, CO (US)

( * ) Notice: Subject to any disclaimer, the term of this patent is extended or adjusted under 35 U.S.C. 154(b) by 957 days.

(21) Appl. No.: 13/578,451

(22) PCT Filed: Feb. 8, 2011

(86) PCT No.: PCT/US2011/024075
§ 371 (c)(1),
(2), (4) Date: Aug. 10, 2012

(87) PCT Pub. No.: WO2011/100253
PCT Pub. Date: Aug. 18, 2011

(65) Prior Publication Data
US 2012/0304743 A1   Dec. 6, 2012

Related U.S. Application Data

(60) Provisional application No. 61/303,388, filed on Feb. 11, 2010.

(51) Int. Cl.
*G01N 31/00*    (2006.01)
*G01N 33/18*    (2006.01)
*G01N 27/02*    (2006.01)

(52) U.S. Cl.
CPC ......... *G01N 33/1846* (2013.01); *G01N 27/02* (2013.01)

(58) Field of Classification Search
CPC .............................. G01N 33/1846; G01N 27/02
(Continued)

(56) References Cited

U.S. PATENT DOCUMENTS 4,626,413 A   12/1986   Blades et al.
5,399,247 A *  3/1995   Carey et al. .................. 205/688
(Continued)

FOREIGN PATENT DOCUMENTS

EP   1927849   6/2008

OTHER PUBLICATIONS

International Searching Authority, Search Report for International Application PCT/US2011/024075, Oct. 26, 2011 (EPO), 2 pages.

*Primary Examiner* — Rebecca M Fritchman
(74) *Attorney, Agent, or Firm* — Ference & Associates LLC

(57) ABSTRACT

A carbon quantifying cell (20) configured to receive a fluid is provided, including two or more electrodes (22) positioned at least partially in the fluid, and meter electronics (21) configured to place an electrical oxidization, polarization, and/or adsorption program across the two or more electrodes (22) and at least partially oxidize carbon materials in the fluid, apply an AC voltage of a predetermined amplitude across the two or more electrodes (22), measuring the resulting AC current across the two or more electrodes (22), wherein a ratio of amplitudes and a phase angle difference provides information for calculating a fluid impedance, receive an electrical response of the fluid to the electrical oxidization, polarization, and/or adsorption program, quantify the carbon materials in the fluid using the electrical response, and detect interfering materials in the fluid using the fluid impedance.

8 Claims, 5 Drawing Sheets

(58) Field of Classification Search
USPC .......................................................... 73/61.41
See application file for complete search history.

(56) References Cited

U.S. PATENT DOCUMENTS

| | | |
|---|---|---|
| 6,444,474 B1 | 9/2002 | Thomas et al. |
| 6,737,276 B1 | 5/2004 | Voss et al. |
| 6,793,889 B2 * | 9/2004 | Naatz ................ G01N 21/71 |
| | | 422/68.1 |

* cited by examiner

CARBON QUANTIFYING APPARATUS AND METHOD

BACKGROUND OF THE INVENTION

1. Field of the Invention

The present invention relates to carbon quantification, and in particular, to a carbon quantifying apparatus and method.

2. Statement of the Problem

Ultrapure water (UPW) is desirable for a variety of industrial processes, particularly pharmaceutical and semiconductor manufacturing. The semiconductor industry uses UPW as a universal solvent in virtually every step of a production process. Typical acceptable conductivity levels for UPW used in semiconductor industries are about 0.05 micro-siemens per centimeter ($\mu S/cm$) and typical acceptable total organic content (TOC) levels are about 1 ppb carbon. Chemical pharmaceutical industries use UPW in the production of drugs and reagents that require high degrees of purity. Typical acceptable conductivity levels for UPW used in pharmaceutical industries can be as high as 1.3 $\mu S/cm$ at 25° C., and typical acceptable TOC levels can be up to 500 ppb carbon.

Ultra low levels of any ionic and non-ionic impurities (or the absence of impurities) therefore are desirable characteristics of UPW. Even small amounts of contaminants or electrolytes can adversely impact the efficacy or yields of the desired products. As semiconductor features decrease in size, smaller amounts of impurities, and certain types of impurities, become less tolerable.

For these reasons, determination of the nature of organic contaminants present in an UPW stream would be desirable and could lead to identification of the contaminant source, as well as remediation of the contaminants, which would be an invaluable cost and time saving tool.

Conventional TOC analyzers measure the amount of $CO_2$ produced when organic carbon-containing molecules are oxidized and/or when inorganic carbon-containing molecules are acidified. TOC analyzers are, therefore, unable to identify the organic molecules in UPW.

Aspects of the Invention

In one aspect of the invention, a carbon quantifying cell configured to receive a fluid comprises:
two or more electrodes positioned at least partially in the fluid; and
meter electronics coupled to the two or more electrodes and configured to place an electrical oxidization, polarization, and/or adsorption program across the two or more electrodes and at least partially oxidize carbon materials in the fluid, apply an AC voltage of a predetermined amplitude across the two or more electrodes, measuring a resulting AC current across the two or more electrodes, wherein a ratio of amplitudes and a phase angle difference provides information for calculating a fluid impedance, receive an electrical response of the fluid to the electrical oxidization, polarization, and/or adsorption program, quantify the carbon materials in the fluid using the electrical response, and detect interfering materials in the fluid using the fluid impedance.

Preferably, the two or more electrodes at least partially comprise a titanium dioxide ($TiO_2$) material.

Preferably, the two or more electrodes at least partially comprise a boron-doped diamond (BDD) material.

Preferably, quantifying the carbon materials includes the meter electronics analyzing the electrical response in order to determine the speciation of the carbon materials and/or speciation of organic materials in the fluid, wherein the speciation detects a presence of carbon material in the fluid.

Preferably, quantifying the carbon materials includes the meter electronics determining an identity of the carbon material in the fluid and determining a quantity of the carbon material in the fluid.

Preferably, quantifying the carbon materials includes the meter electronics determining relative fractions of two or more carbon materials in the fluid.

Preferably, the electrical oxidization, polarization, and/or adsorption program includes one or more of a predetermined DC voltage profile, a predetermined AC voltage profile, or a predetermined current profile.

Preferably, placing the electrical oxidization, polarization, and/or adsorption program across the two or more electrodes further comprises applying a varying DC voltage program across the two or more electrodes, thereby preferentially adsorbing and/or oxidizing and/or polarizing a predetermined carbon solute.

In one aspect of the invention, a method for quantifying carbon materials in a fluid comprises:
placing an electrical oxidization, polarization, and/or adsorption program across two or more electrodes positioned at least partially in the fluid and polarizing and/or adsorbing and/or at least partially oxidizing the carbon materials in the fluid;
applying an AC voltage of a predetermined amplitude across the two or more electrodes;
measuring a resulting AC current across the two or more electrodes, wherein a ratio of amplitudes and a phase angle difference provides information for calculating a fluid impedance;
quantifying the carbon materials in the fluid using an electrical response of the fluid to the electrical oxidization, polarization and/or adsorption program; and
detecting interfering materials in the fluid using the fluid impedance.

Preferably, quantifying the carbon materials includes analyzing the electrical response in order to determine the speciation of the carbon materials and/or speciation of organic materials in the fluid, wherein the speciation detects a presence of carbon material in the fluid.

Preferably, quantifying the carbon materials includes determining an identity of the carbon material in the fluid and determining a quantity of the carbon material in the fluid.

Preferably, quantifying the carbon materials includes determining relative fractions of two or more carbon materials in the fluid.

Preferably, the electrical oxidization, polarization, and/or adsorption program is maintained for at least a predetermined polarization time period without oxidation of the organic species.

Preferably, the electrical oxidization, polarization, and/or adsorption program is maintained for at least a predetermined adsorption time period without oxidation of the organic species.

Preferably, the electrical oxidization, polarization, and/or adsorption program includes one or more of a predetermined DC voltage profile, a predetermined AC voltage profile, or a predetermined current profile.

Preferably, the electrical oxidization, polarization, and/or adsorption program includes applying a varying DC voltage program across the two or more electrodes, thereby preferentially adsorbing and/or oxidizing and/or polarizing a predetermined carbon solute.

In one aspect of the invention, a method for quantifying carbon materials in a fluid comprises:
  applying an AC voltage of a predetermined amplitude across the two or more electrodes;
  measuring a resulting AC current across the two or more electrodes, wherein a ratio of amplitudes and a phase angle difference provides information for calculating a fluid impedance;
  applying a varying DC voltage program across the two or more electrodes, thereby preferentially adsorbing and/or oxidizing and/or polarizing a predetermined carbon solute;
  quantifying the carbon materials in the fluid using an electrical response of the fluid to the electrical oxidization, polarization and/or adsorption program; and
  detecting interfering materials in the fluid using the fluid impedance.

Preferably, quantifying the carbon materials including analyzing the electrical response in order to determine the speciation of the carbon materials and/or speciation of organic materials in the fluid, wherein the speciation detects a presence of carbon material in the fluid.

Preferably, quantifying the carbon materials including determining an identity of the carbon material in the fluid and determining a quantity of the carbon material in the fluid.

Preferably, quantifying the carbon materials including determining relative fractions of two or more carbon materials in the fluid.

DESCRIPTION OF THE DRAWINGS

The same reference number represents the same element on all drawings. It should be understood that the drawings are not necessarily to scale.

DETAILED DESCRIPTION OF THE INVENTION

FIGS. 1-7 and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention. Those skilled in the art will appreciate that the features described below can be combined in various ways to form multiple variations of the invention. As a result, the invention is not limited to the specific examples described below, but only by the claims and their equivalents.

Figure 1:
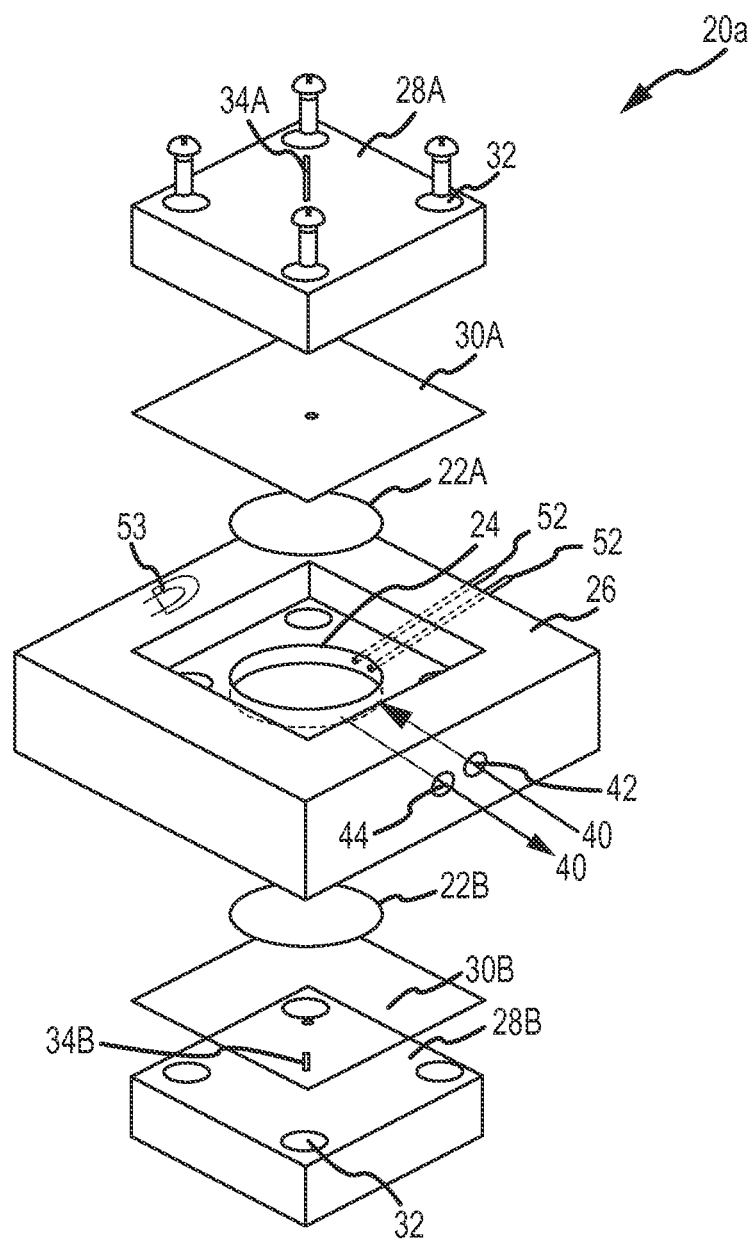
FIG. 1 is an exploded view of a carbon quantifying cell according to an embodiment of the invention.

FIG. 1 is an exploded view of a carbon quantifying cell according to an embodiment of the invention. The carbon quantifying cell 20 may be used for speciation of organic materials in a fluid. Two or more electrodes 22 are positioned at least partially in the fluid. The electrochemical cell 20 includes a supporting body 26 including a cavity 24. The electrochemical cell 20 further includes two cover plates 28A and 28B that are configured to be assembled to the supporting body 26 and close off the cavity 24. An inlet 42 and an outlet 44 communicate between the cavity 24 and the exterior, wherein fluid may flow into and out of the cavity 24 (see arrows 40, for example). Fluids are received in the cavity 24 and tested therein.

The cavity 24 and the supporting body 26 may be made from polytetrafluoroethylene (PTFE) in some embodiments, or any suitable material coated by PTFE. Skilled persons will appreciate that other materials and coating can be used.

Insulators 30A and 30B are positioned between the supporting body 26 and the cover plates 28A and 28B. Electrodes 22A and 22B are held inside the cavity 24. Electrodes 22A and 22B may be received on shoulders or in grooves in the cavity 24 (not shown). The insulators 30A and 30B are positioned so that the electrodes are electrically isolated from the cover plates 28A and 28B. The electrodes 22A and 22B are in contact with electrical leads 34 that pass through the cover plates 28A and 28B and through the insulators 30A and 30B. Consequently, an electrical field can be placed across the two electrodes 22A and 22B, wherein a resulting electrical current can be generated through the fluid under test.

The electrochemical cell 20 can further include a UV source 53 in some embodiments. The UV source 53 can be positioned to transmit UV light into the cavity 24, such as through a UV translucent panel (not shown). The UV light can radiate into the cavity 24 and interact with the fluid. For example, the UV light may initiate, cause, enhance, accelerate, or otherwise participate in oxidization of the fluid and material within the fluid.

The electrochemical cell 20 can include a thermistor 52 in some embodiments. The thermistor 52 can be positioned to measure a temperature of the cavity 24. The temperature measurements can be used in analyzing the fluid and the material within the fluid. The thermistor 52 can measure the before, during, and after the application of direct current (DC) voltage and during impedance measurement.

The electrochemical cell 20a may employ specialized electrodes, such as metal oxides or modified or unmodified doped diamond electrodes, to selectively oxidize and sense organic compounds in water streams, such as those of manufacturing processes.

The electrochemical cell 20 can be used to perform online measurements to determine organic compound speciation and TOC, if desirable. The online speciation can be performed in either a flow mode or stopped flow mode in the cavity 24.

The cover plates 28 can be made from aluminum or stainless steel, for example, and may be threaded with holes to receive screws 32 for assembling the electrochemical cell 20. The electrodes 22 may be connected through the electrical leads 34 to an external power supply that may be used for applying a voltage program to the electrodes 22 in the electrochemical cell 20.

A sample UPW solution that may contain one or more organic impurities or analytes may be directed in a flowing stream, or diverted from a stream, in a flow direction 40 through an inlet 42 into the electrochemical cell 20 and through an outlet 44 that leads back to the fluid stream, to one or more additional electrochemical cells 20, or to a waste stream. While in the electrochemical cell(s) 20, the sample solution is exposed to the electrodes 22. A voltage program can then be applied that causes only a specific molecule or class of molecules to adsorb to the electrode and then undergo an oxidation-reduction (redox) process.

An alternating current (AC) field superimposed on the voltage program may allow concurrent impedance detection during the adsorption and electrochemical process. Impedance, conductivity, and/or resistance can also be measured by separately applying the AC field, including applying the AC field before, after or during the voltage program. The conductivity, resistance and/or impedance-potential profiles obtained can be used as a "fingerprint" to differentiate organic species. Alternatively, a current program may be applied to the electrodes 22 for oxidation and/or adsorption purposes and the voltage is measured between the additional electrodes 52 in contact with the UPW.

In some embodiments, the voltage measurement electrodes 52 are made from a metal or alloy such as stainless steel stainless steel and/or titanium. An electrochemical cell 20 having four electrodes (two of each type, oxidation and measurement electrodes) may reduce possible in-situ impedance measurement errors caused by any undesirable bubble formation during the oxidation process. AC impedance can be measured before, after and during the oxidation of the sample by UV radiation.

A DC voltage program is applied to the two electrodes 22 for oxidizing any organic compounds within a fluid. Impedance is measured before, after and during the DC voltage program by applying a superimposed AC voltage.

In operation, a fluid to be tested is admitted into the cavity 24. The fluid can be flowing or static, as previously discussed. A voltage program is applied to the electrodes 22A and 22B in order to oxidize the fluid and material within the fluid. Characteristics of the applied electrical voltage, and the resulting electrical current, may be tracked and logged. Further, an AC voltage may be applied in order to measure an impedance of the fluid and the AC voltage and/or AC current can be tracked and logged. The resulting electrical response information may be analyzed in order to detect organic materials in the fluid and in order to speciate the organic materials (i.e., determine the species of organics present).

In some embodiments, the electrochemical cell 20 and associated meter electronics may be configured to place an electrical oxidization program across electrodes positioned at least partially in the fluid and at least partially oxidizing the carbon materials in the fluid, quantify the carbon materials in the fluid using an electrical response of the fluid to the electrical oxidization program, and detect interfering materials in the fluid using the electrical response.

Electrochemical selectivity techniques that have been used to determine the nature of some organic contaminants in aqueous solutions have been investigated. Such electrochemical techniques require various concentrations of electrolytes to conduct the analysis. In particular, conventional electrochemical systems achieve selective oxidation by scanning or stepping a DC voltage across a predetermined voltage range in presence of electrolytes (typically 100 mill molar). Organic identification is achieved by measuring the current generated due to oxidation of the organic compounds. This oxidation-generated current is known as Faradaic current which can be detected against a small background charging current (due to charging of the electrodes) that is present in all electrochemical systems. The charging and background currents may be small due to the presence of electrolytes.

Because of the high resistance (18.2 M$\Omega$ cm) of UPW, a large background charging current would be present in UPW systems. Therefore, obtaining a meaningful Faradaic current that is separated from the large background current during the electrochemical oxidation of parts-per-billion (ppb) levels of organic compounds in UPW samples would be extremely difficult. These electrochemical techniques cannot work under low electrolyte or no electrolyte conditions. As a result, there is no cost effective technique for on-line electrochemical TOC speciation, such as detecting ppb organic analytes in ultrapure de-ionized water samples.

An organic impurity analyzer or TOC analyzer with speciation capabilities therefore would provide significant advantages over existing TOC analyzers, especially for on-line analyses.

Some embodiments for effecting electrochemical speciation of ppb-level organic compounds in UPW samples (especially samples with low or no electrolyte content) may include, but are not limited to, one or more of the following techniques: using metal or metal oxide electrodes, doped-metal oxide electrodes, doped-mixed metal oxide electrodes, or doped-diamond electrodes, using any of the disclosed embodiments to selectively adsorb, pre-concentrate and oxidize the organic compounds; implanting, doping or electrodepositing metals or metal oxides on inert substrates like titanium dioxide or doped-diamond substrate for selective adsorption and/or oxidation of organic molecules; performing organic or TOC speciation based on the rate and/or energy of organic oxidation; using specialized geometries of the sensing and/or oxidizing electrodes to provide a well-defined relationship between the electrodes to facilitate analytical electrochemistry in high resistance media (the electrode geometries in conventional TOC applications are of little consequence); employing a compact design of an electrochemical cell to enable efficient online and real-time detection and quantification of organic compounds; providing DC and/or AC voltage programs to facilitate measurement of the interfacial, bulk, and/or diffusional impedance of the electrochemical cell to obtain online species specific information about the TOC in high resistance media; or measuring the TOC on modified or unmodified doped-diamond electrodes during and after speciation.

In some embodiments the electrode design, such as a close parallel arrangement of the electrodes, may limit the voltage drop caused by the high resistance media such as UPW, may efficiently expose the organic compounds to the electrodes, and may displace bubbles that might otherwise be formed at the electrode/solution interface. In some embodiments, microelectrodes or metal regions implanted on an inert substrate like doped-diamond substrate may enhance electrochemical detection. In some embodiments, selective adsorption and/or pre-concentration of organic molecules using modified doped-diamond electrodes may enhance detection.

In some embodiments, monitoring the variation of the electrochemical cell's impedance during oxidation/adsorption of the organic molecules may be an efficient detection method in a high resistance system like UPW. In some embodiments, employing in-situ impedance as a detection method may facilitate use of fewer sensors. Fewer inert metal oxide/metal electrodes can suffice for detecting various families/classes of organic molecules using impedance techniques. If conventional electrochemical techniques are used, then each family or each organic compound should need an individual sensor for detection purposes.

In some embodiments, stopped flow and/or flow techniques can be used to expose the sample solution to the electrodes.

In some embodiments, electrochemical speciation may include analysis without the addition of electrolytes or reagents.

In some embodiments, electrochemical speciation can be determined in the absence of a TOC measurement.

Figure 2:
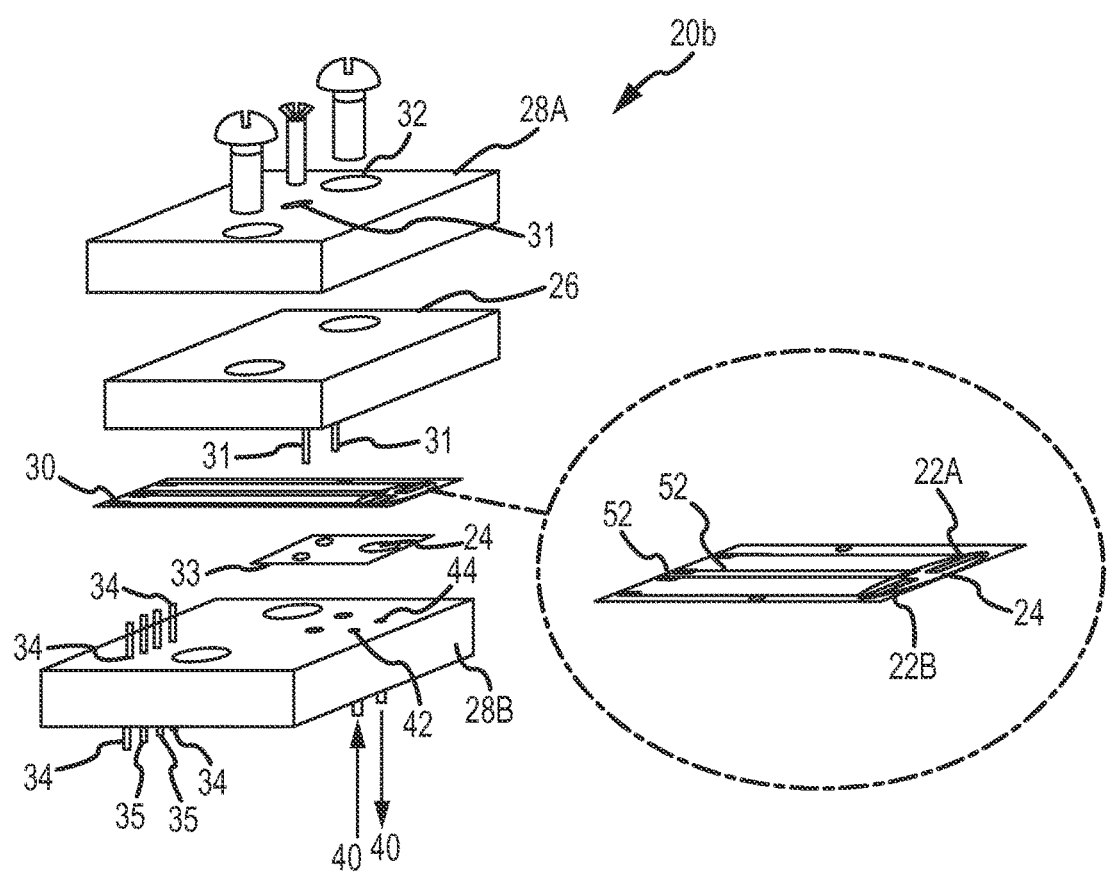
FIG. 2 shows a carbon quantifying cell having replaceable and/or disposable thin film electrodes according to an embodiment of the invention.

FIG. 2 shows a carbon quantifying cell 20 having replaceable and/or disposable thin film electrodes 22A and 22B according to an embodiment of the invention. The disposable thin film electrodes 22A and 22B can be used to measure in-situ impedance of the electrochemical cell 20 during, before and after a DC voltage program. The insulating material 30 has guide pins 31 in this embodiment. These guide pins are used to align the position of the electrodes with the inlet and outlet of the electrochemical cell. The insulator 30 is used to hold the electrodes 22A and 22B and the thermistor 52. Electrodes 22A and 22B, and optionally thermistor 52, can be produced on the insulator 30 by screen printing, laser ablation, electrodeposition, chemical vapor deposition, chemical bath deposition or other techniques. The electrodes 22A and 22B are designed to adsorb, oxidize and measure the organic molecules. Gasket 33 is made of inert material like PTFE and is used to seal the cover plates 28A and 28B to the supporting body 26 and complete the cavity 24, where the sample is exposed to the electrodes 22A and 22B. The guide pins 31 maintain the position of the flexible substrate 30 and the gasket. The electrodes 22 may be connected through the electrical leads 34 to an external supply and monitor that may be used for applying a voltage program to the electrodes 22 and measure the current response in the electrochemical cell 20. The thermistor 52 may be connected through the electrical leads 35 to an external meter that may be used to monitor the temperature of the contents of the cell.

Figure 3:
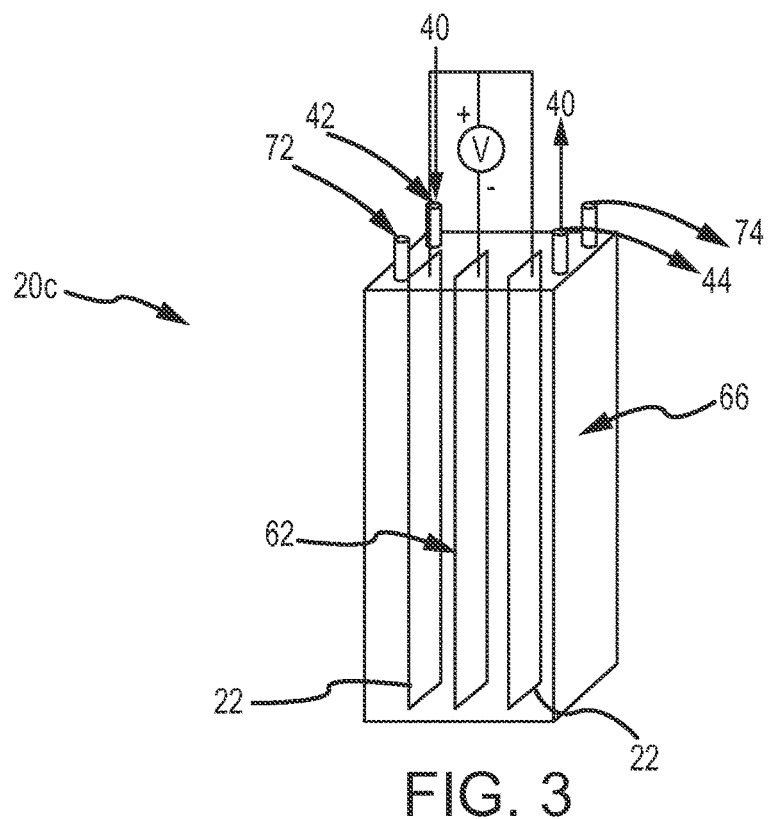
FIG. 3 shows a carbon quantifying cell having three electrodes according to an embodiment of the invention.

FIG. 3 shows a carbon quantifying cell 20c having three electrodes according to an embodiment of the invention. The carbon quantifying cell 20c can be used for online speciation of organic compounds. The electrochemical cell 20c includes two working electrodes (anodes) 22 and a counter electrode (cathode) 62 housed within a quartz or glass cell 66 that functions like the body 26 to contain moving or stationary samples of UPW that may contain organic impurities. Other materials known to skilled practitioners may be used to form the cell 66. It is preferable to use inert materials like quartz, titanium or diamond as the material which is in contact with the sample solution. The material which is not in contact with the sample can be produced with any convenient material.

In some embodiments, in addition to the inlet 42 and the outlet 44 for the UPW samples, the electrochemical cell 20c has an inlet 72 and an outlet 74 to support the flow of nitrogen or an inert gas through, or the containment of the gas within, the electrochemical cell 20c to prevent atmospheric contamination. As with the other embodiments of electrochemical cells, a DC voltage with a superimposed AC voltage can be applied.

In some embodiments, the electrodes 22 are arranged in a close and generally parallel configuration or planar configuration. In general, the electrodes 22 are spaced far enough apart to ensure electrical isolation and close enough together to minimize the voltage drop across the electrodes 22 because of the high resistance of UPW (e.g., 18.2 MΩ cm). In particular, the DC voltage applied to the electrodes for oxidizing and detecting the organic species may largely depend on distance between the electrodes in a high resistive media like UPW. The voltage drop across the electrode decreases with a decrease in the distance between the electrodes 22. However, if the distance between the electrodes 22 is too small, then exposure of the organic compound impurities to the electrodes would be less efficient. Hence, an optimal distance between the electrodes 22 is desirable to minimize the voltage drop and maximize delivery of organic compounds to the electrodes 22.

In some embodiments, the distance between the electrodes 22 is within a range of about 0.1 mm to about 1 cm. More preferable spacing distances are within a range of about 0.1 mm to about 2 mm. In some embodiments, the distance between the electrodes 22 is within a range of about 1 mm to about 2 mm. In some embodiments of FIG. 1, the distance between the electrodes 22 is 1-2 mm. In some embodiments of FIG. 2 the distance between the electrodes 22 is fixed at 0.1 mm or 1 mm. In some embodiments of FIG. 3, the distance between the electrodes 22 is fixed at about 1 mm.

The preferred distance or range of distances between electrodes may also vary as a consequence of one or more of the dimensions, surface area, and composition of the electrodes 22 or the nature of the electrode coatings as well as may vary as a consequence of one or more of the amount of the ranges of applied voltage or current, the amount of expected organic impurities, the flow rate of the samples through the electrochemical cell 20, the geometry of the electrochemical cell 20, and the particular application of the electrochemical cell 20.

In general, larger surface areas and smaller distances for the electrodes 22 enhance the signals obtained during interfacial measurements and enable measurements of very low concentrations of organic molecules in UPW. The dimensions of the working electrodes 22 may be the same size as each other and the same size as the non working or counter electrode 62, or one or more of the electrodes 22 or 62 may be different sizes. The preferred dimensions or range of dimensions of electrodes may also vary as a consequence of one or more of the spacing, surface area, and composition of the electrodes 22 or the nature of the electrode coatings as well as may vary as consequence of one or more of the amount of the ranges of applied voltage or current, the amount of expected organic impurities, the flow rate of the samples through the electrochemical cell 20, the geometry of the electrochemical cell 20, and the particular application of the electrochemical cell 20.

In some exemplary embodiments, one or more electrodes 22 have an active or coated surface area within a range of about 0.0001 $cm^2$ to about 100 $cm^2$. In some exemplary embodiments, one or more electrodes 22 have an active or coated surface area within a range of about 0.1 $cm^2$ to about 100 $cm^2$. In some exemplary embodiments, one or more electrodes 22 have an active or coated surface area within a range of about 0.0001 $cm^2$ to about 0.1 $cm^2$. In some exemplary embodiments, one or more electrodes 22 have an active or coated surface area within a range of about 0.01 $cm^2$ to about 10 $cm^2$.

In some embodiments, the electrodes 22 have dimensions of about 1 cm diameter and 0.2 mm thick to about 3 cm diameter 0.2 cm thick to are coated on one or both sides, and have an electrode surface area exposed to the solution of about 1.5 $cm^2$ to about 10 $cm^2$. In some embodiments of FIGS. 1-3, the electrodes 22 have dimensions of 1 cm diameter by 0.2 cm thick and are coated on one side and have an electrode surface area exposed to the solution of about 1.5 cm². In some embodiments of FIGS. 1-3, the electrodes 22 have dimensions of 1 cm diameter and 0.2 cm thick and are coated on both sides such that an embodiment of FIG. 1 would have an electrode surface area exposed to the solution of about 6 cm² and an embodiment of FIG. 3 would have an electrode surface area exposed to the solution of about 12 cm². In some embodiments of FIG. 3, the working electrode 22 has an electrode surface area exposed to the solution of about 10 cm² and the counter electrode 62 has an electrode surface area exposed to the solution of about 5 cm².

In some embodiments, each electrode 22 is coated on only a single side (monopolar), the surface area of each electrode 22 is 0.84 cm², and the distance between the electrodes is 1 to 2 mm. In some embodiments, each electrode 22 and 52 are coated on both sides (bipolar), the surface area of each electrode 22 is 10 cm², the surface area of the counter electrode 52 is 5 cm², the distance between the electrodes 22 and 52 is 1 to 2 mm, and the volume of the electrochemical cell 20c is 2 mL.

Skilled persons will appreciate that numerous combinations of electrode spacing, dimensions, surface area, composition, and coating and electrochemical cell 20, geometry are possible and are contemplated. The examples given herein are given merely for illustration and the carbon quantifying cell 20 is not limited by any of the included examples. Additionally or alternatively, a microelectrode array (not shown) containing hundreds or even thousands of micron-sized electrodes may be employed. Such a microelectrode array can be employed in an electrochemical cell 20 such as in a UPW supply stream, or such a microelectrode array can be dipped in a sample solution containing an organic compound for oxidation and detection. In some embodiments, the microelectrode arrays may be employed in the form of interdigitated arrays (IDAs) or interdigitated ultramicroelectrode arrays (IDUAs) with uniform distances between the electrodes in a generally coplanar fashion. In an exemplary embodiment, a microelectrode array may include 106 electrodes that are about 5 μm in diameter and that are spaced about 150 μm away from each other.

Each array of electrodes 22 may contain only identical electrodes 22 or a one or more different electrodes 22 having one or more different properties of electrode spacing, dimensions, surface area, composition, or coating.

Additionally or alternatively, electrochemical cells 20 or arrays of electrodes 22 may be positioned in series in an UPW flow stream. Such electrochemical cells 20 or arrays of electrodes 22 may have the same or different configurations or properties. For example, each electrode 22 could be modified with different active materials, such as conducting polymer or active metals like Cu, Pt, as later described.

Another exemplary alternative embodiment employs concentric mesh electrodes 22 that provide a high surface area and a tendency to minimize the trapping of bubbles. Such mesh electrodes 22 may employ porous titanium dioxide or diamond substrates such that the UPW fluid can flow through the electrodes 22 during the selective oxidation/adsorption process.

Another exemplary alternative embodiment of an electrochemical cell or system 20 employs a concentric hollow tube with a solid cylinder at the center of it to maximize the surface area of the electrodes 22. The UPW fluid that may contain organic analyte impurities flows between the cylinder and the hollow tube. The inner part of the hollow tube may be coated with a $TiO_2$ or boron-doped diamond (BDD) material, which is described later. In some embodiments, an exemplary distance between such concentric electrodes 22 can be within the range from 0.1 mm to 1 cm. Skilled persons will once again recognize that numerous alternative variations are possible, especially in view of the number of discussed variables.

In some exemplary embodiments, the UPW fluid containing the analyte is trapped or flowed between the electrodes 22 at a rate in the range of 0.16 mL/min to 16 mL/min. Some exemplary electrochemical cells 20 have a cell volume of about 2 mL. In embodiments where flowing conditions are used, the flow rates required to oxidize the most difficult organic is identified. This is used as a standard to measure the impedance before, after and during the oxidation. The flow rate may depend on a number of factors, such as one or more of the particular application, electrochemical cell geometry, or electrode parameters.

In some embodiments, the electrodes 22, 52, and 62 (collectively electrodes 22) may be made from $TiO_2$ or BDD material. The BDD electrodes 22 contain a thin polycrystalline diamond layer on a conductive substrate material. BDD coatings are a relatively new material for the electrodes 22 and exhibit exceptional chemical stability as well as high wear resistance. The BDD electrodes 22 also exhibit high oxygen and hydrogen over-potentials. The electrochemical window in which meaningful processes can be observed is governed by the reduction and oxidation of the solvent. In this invention, primarily water is the solvent in which organic speciation is performed. The reduction of water produces hydrogen, and oxidation of water produces oxygen. The energy required to oxidize or reduce water strongly depends on the electrode substrate. On inert BDD electrodes, the energy required to produce oxygen and hydrogen is relatively higher than most of the electrodes in aqueous solvents. This results in very low background noise, which is another attractive feature of BDD electrodes.

Figure 4:
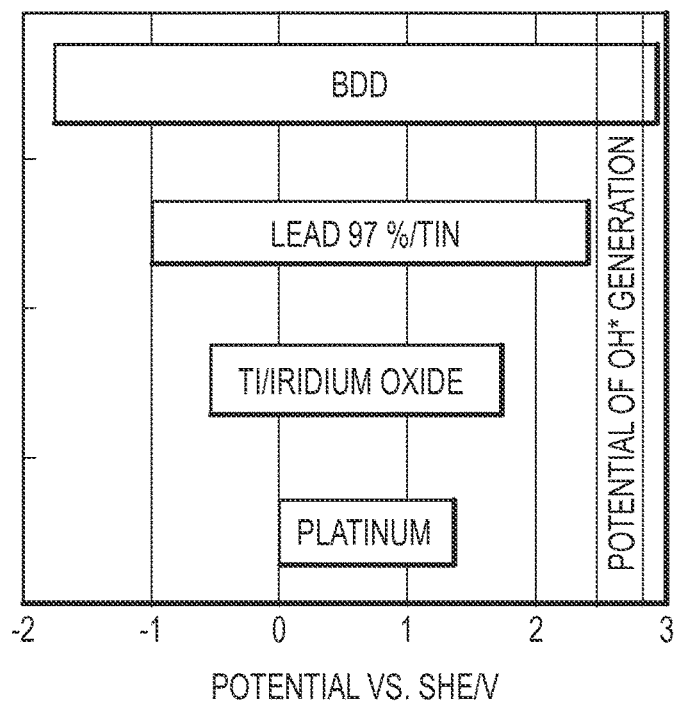
FIG. 4 is a graph showing the electrochemical stability of boron-doped diamond electrodes versus other representative conventional electrodes.

With reference to FIG. 4, the BDD electrodes exhibit the greatest electrochemical stability. This figure shows the electrochemical window of various electrode materials. BDD clearly has the largest electrochemical window. The hydrogen and oxygen evolution occurs outside the horizontal bars indicating the electrode material.

FIG. 4 is a graph showing the electrochemical stability of BDD versus other representative conventional electrodes. Electrodes that are comparable to BDD include doped and undoped iridium oxide ($IrO_2$) electrodes, tin oxide ($SnO_2$) electrodes, antimony oxide ($Sb_2O_5$) electrodes, lead dioxide ($PbO_2$) electrodes, niobium or tantalum doped titanium dioxide ($Nb/TiO_2$ or $Ta/TiO_2$) electrodes, and dimensionally stable anodes (DSA), typically stable metal alloys and $TiO_2$. Any of these electrode materials may be suitable for use as electrodes 22 in many of the embodiments and applications discussed herein.

The BDD electrodes 22 evoke particularly low background noise, a property which is especially useful for obtaining meaningful electrochemical signals arising from the oxidation or adsorption of the organic compounds in UPW. The BDD electrodes can be selectively modified to enhance selectivity for particular organic groups or compounds, as later discussed.

An embodiment of an exemplary electrode 22 may include a base material of niobium or any other suitable metal or alloy. An exemplary thickness of the base material is about 2 mm, but the thickness may be changed to suit the variables previously mentioned and/or manufacturing considerations. An exemplary thickness of the diamond coating is within a range of about 1 to 20 μm. An exemplary standard thickness is about 5 µm with homogeneity of ±10%. An exemplary boron doping level is within a range of about 100 to 8000 ppm. In some exemplary embodiments, the boron doping level is about 1019-1021 boron atoms per $cm^3$.

An exemplary resistivity of an electrode 22 may be within the range of about 10 to 100 mΩ cm, with current density limitations up to about 500 mA $cm^{-2}$. The BDD may be coated on one or all the sides of the niobium substrate (bipolar BDD electrodes). An exemplary distance between the electrodes 22 tailored to these parameters is about 1 to 2 mm.

Modifying BDD can impart selectivity to produce functionalized BDD electrodes 22. Such functionalized BDD electrodes 22 can be prepared by several methods. Implanting, or electrochemical deposition of BDD with active materials in the form of metals, such as copper (Cu), nickel (Ni), or platinum (Pt), palladium (Pd), silver (Ag), ruthenium (Ru), zinc (Zn), or metal oxides, such as cupric oxide (CuO) or iridium oxide ($IrO_2$), can provide means for selective detection of organic molecules. The implanted active material acts as a microelectrode on BDD. Due to the difference in diffusion processes between the microelectrode(s) and "macro" electrode 22 selective detection is possible.

For example, Ag modified BDD electrodes 22 are selective towards amines; $IrO_2$ modified BDD are selective towards alcohols; Zn modified BDD are selective towards trihalomethanes, and ionic molecules like organic acids can be identified by measuring the change in the bulk conductivity without any modifications to the BDD. Bulk conductivity can be directly obtained from the impedance measurements as later discussed.

BDD can also be modified with functionalized polymers, which can be tuned to impart selectivity towards specific organics. Oxidation/reduction of the BDD substrate in the presence of desired functional groups can introduce the functional groups directly on to the BDD substrate. These functional groups can selectively react with organic compounds. The selection of the functional groups can be tailored to reactions with known or anticipated organic contaminants.

Organic compounds commonly found in UPW include urea, carboxylic acids, such as formic acid or acetic acid; resin amines or their derivatives, such as trimethyl amine or trimethyl ammonium hydroxide, alcohols, such as isopropyl alcohol or methanol, and trihalomethanes, such as chloroform. Table I presents a list organic compounds and classes of compounds and electrode modifications for selectively detecting them.

TABLE I

Electrode Modifications for Selective Detection of Organic Compounds

| Organic compounds | Metals/metal oxides/conductive polymers |
|---|---|
| Urea | Titanium/platinum-iridium$_{(70:30::Pt:Ir)}$, titanium/(tantalum oxide or iridium oxide)70:30, platinum, enzyme modified poly-thiophene |
| Carboxylic acids | Tin/tungsten oxide, titanium/tin oxide, lead oxide, ruthenium oxide, polypyrrole, titanium suboxide (Ebonex) |
| Amines | Silver-lead oxide, silver-lead alloys |
| Alcohols | Copper (II) oxide, cobalt (III) oxide, cobalt (IV) oxide/hydroxide, iridium oxide, silver oxide, platinum, poly-N (2-pyridyl pyrrole) |
| Trihalomethanes | Zinc, platinum, gold, silver, zinc (II) porphyrin polyaniline, poly (o-ethoxyaniline, poly(3,4-diphenylpyrrole) |

In some embodiments, a series or array of electrodes 22 or microelectrodes, in which each BDD electrode is modified with different active materials (different conductive polymers, different active metals, and/or different active metal oxides), can be used to cover a wide range of organic compounds that may be present as impurities. Similarly, the same or different electrodes 22 may be subjected to the same or different DC and/or AC voltage programs including the same or different voltages, waveforms, frequencies, increments, and/or timing schemes.

All these approaches can be tailored to selectively detect and/or quantify specific organic compounds at ppb levels in a mixture of organic compounds in UPW by measurement of interfacial and bulk properties of the electrochemical cells 20 with or without application of DC voltages.

DC voltage can be applied to the electrodes to oxidize organic molecules or to enhance the interaction between organic molecules and the electrodes 22. Application of specific voltages oxidizes or facilitates the adsorption of specific organics. Hence by varying DC voltages, specific organic compounds or specific classes of organic compounds can be oxidized or adsorbed selectively. The electrode geometries discussed permit on-line analysis in the absence of reagents or electrolytes and permit very small signals arising from oxidation and/or adsorption of ppb levels of organic molecules.

In addition, functionalized electrodes 22 can spontaneously adsorb specific organic compounds without the application of DC voltage. This adsorption will cause a change in the interfacial properties. Measuring the interfacial properties of the electrochemical cell 20 will provide qualitative and quantitative information about specific organic molecules present in the electrochemical cell 20.

In particular, impedance measurement techniques can be used to discriminate organic species in UPW. In some embodiments, a single impedance measurement can be used to obtain various interfacial and bulk parameters of an electrochemical system or cell 22. Obtaining various parameters such as interfacial capacitance, charge transfer resistance (Rct), surface potential, solution resistance, phase angle, dielectric property, dissipation factor, and bulk capacitance with a single impedance scan and measurement can provide unique 2D and 3D profiles for specific organic compounds. The organic species can be both quantified and identified by such an approach.

Double layer/series/interfacial capacitance, an interfacial parameter, arising from the electrostatic, adsorption or charge stored at the heterogeneous interface between solid electrode and liquid sample solution, can be determined by measuring the impedance quantities. Heterogeneous charge transfer resistance is another interfacial parameter which arises from the resistance encountered by the charge which is transferring from the electrode (solid phase) to the solution (liquid phase). When a metal oxide semiconductor ($TiO_2$) is used a the electrodes, 22, charge separation occurs and confines to the surface of the electrode. This causes a surface potential to develop. This potential can be calculated by determining the charge stored at the interface by impedance measurement. Solution resistance can be determined by applying an appropriate frequency to the electrodes, which eliminates other interfering electrical parameters and can be easily measured by impedance techniques. Phase angle between the applied AC voltage and the measured AC current will provide information of the capacitive components and the resistive components present in the electrochemical cell. The dissipation factor of the system is the ratio of the energy dissipated by a system due to resistive heating to the energy stored by the system by capacitive and inductive mechanisms. The dissipation factor reaches a maximum when the energy stored by the capacitive/inductive mechanism tends to be zero. At high frequencies (10 MHz to 1 GHz) a maxima is observed for the dissipation factor. This impedance quantity can be determined by applying high frequencies. The capacitance of the sample solution depends on the dielectric properties of the solution. The dielectric properties depend on the nature of the species.

In some embodiments, DC voltages (or DC voltage ranges) in a wide range of potential from about 0 to about 100 V can be used for samples containing a mixture of organic impurities. For some embodiments, various fixed DC voltages within the range of 0 to 10 V can be used.

Depending on flow rate, the DC voltage can be slowly continuously increased (or decreased) or stepped up (or down) in gradual increments or jumped to specific voltages or voltage ranges where known impurities can be identified. In some embodiments, the increment of DC voltage may be within the range of about 0.01 V to 1 V. In some embodiments, the increment of DC voltage may be about 0.05 V. The increment values may be influenced by the size of the DC voltage range and predetermined voltage differentiation points. The increment values need not be the same and any subsequent voltage increment may be smaller or larger in size than a previous voltage increment.

In some voltage stepping embodiments, the voltage may be maintained at each voltage level for a period within the range of about 10 seconds to about 10 minutes subject to flow rates and other considerations. Such considerations include, but are not limited to, the parameters of the superimposed AC current program including its waveform, range of frequencies, and duration of each frequency.

In some embodiments, the voltage at each step may be maintained for a period within a range of about 1 minute to about 5 minutes. The voltage at each step need not be maintained for the same period of time. For example, steps at voltages where distinctive data for common organic impurities can be obtained may be maintained for longer periods of time than for steps at voltages where data for rare or unknown organic impurities may be obtained. One or more libraries of electrochemical data for each type of organic impurity with each type of electrode 22 or modified electrode 22 and/or electrochemical cell 20 can be developed over time so that the voltage programs can be tailored to be as quick and efficient as possible. The voltage program can be adjusted by an operator or automatically adjusted when samples exhibit changes in the nature of the organic impurities.

In some embodiments, a fixed DC current may be applied from within an exemplary range of 0.001 mA to 10,000 mA. In some embodiments, the fixed DC may be within a range of 0.001 mA/s to 100 mA/s. In some embodiments, the DC may be applied in a stepped linear ramp between 0.001 mA/s to 100 mA/s. This type of profile can be used in a four electrode system, for example, where DC current can be applied between the first set of electrodes 22 and the voltage developed across the system can be measured by the second set of electrodes 52.

In some embodiments, AC amplitudes or amplitude ranges in a wide range of potential from about 0 to about 100 V can be used, and various frequencies or frequency ranges within a range of 0.001 Hz to 1 GHz of an AC sine wave, with or without a fixed DC base voltage, can be used to establish and detect the impedance profiles. In some embodiments, AC amplitudes or amplitude ranges in a range of potential from about 0 to about 10 V can be used with various frequencies or frequency ranges within a range of 0.001 Hz to 1 GHz of an AC sine wave. In some embodiments, AC amplitudes or amplitude ranges in a range of potential from about 0 to about 10 V have been used with various frequencies or frequency ranges within a range of 10 Hz to 100 Hz of an AC sine wave.

The frequency of the AC waveform can be slowly continuously increased (or decreased) or stepped up (or down) in gradual increments or jumped to specific frequencies or frequency ranges where known impurities can be identified. In some embodiments, the increment of AC waveform frequency may be within the range of about 0.001 Hz to 1000 Hz. In some embodiments, the increment of AC waveform frequency may be about 10 Hz. The increment values may be influenced by the size of the AC waveform frequency range and predetermined frequency differentiation points. The increment values need not be the same and any subsequent frequency increment may be smaller or larger in size than a previous frequency increment.

Other AC waveforms could be employed such as square waveforms, triangle, saw tooth, or differential square wave ramp waveforms. Furthermore, more than one AC waveform may be tested at any given AC or DC voltage.

For some exemplary embodiments, an AC sine waveform of 0.005 V amplitude with fixed frequencies within a range of 10 Hz to 100 KHz has been superimposed on various fixed DC voltages in the range of 0 to 10 V to detect selective organic compounds.

In some experiments concerning exemplary embodiments, the DC voltage was applied in increments of 0.05 V from an initial potential of 0 V to a final potential of 10 V. A sequential AC sine waveform of 0.005 V amplitude was superimposed on the base DC potential. The frequency was fixed at 10 Hz. The current and potential were sampled and analyzed to obtain real and imaginary impedance. The experiments show that the resultant impedance-potential profiles are unique for different organic acids in ultra pure water in cell 20a and 20c.

In one set of experiments, a fixed base DC voltage was applied typically for 2 minutes while the AC voltage of amplitude 5 mV at a fixed frequency of 10 Hz was superimposed on the base DC voltage.

In another set of experiments, the DC voltage was scanned from 0 to 10 V in increments of 0.05 V. The AC voltage of amplitude 5 mV at 10 Hz was superimposed on the base DC voltage. In this set of experiments, after each increment of the DC voltage, the CH instrument 760 C potentiostat was operated to wait for a stable response and measure the AC current. This measurement was used to calculate the impedance parameters. The duration for one scan between DC voltages 0 and 10 was 3 minutes at a frequency of 10 Hz.

The applied frequency affected the duration of the experiments and affected the duration of the steps and scam in general. Typically the duration of the experiments was shorter for higher frequencies and was longer for lower frequencies. At lower frequencies the instrument takes a longer time to produce a stable measurement.

Ion chromatographs were obtained to confirm selective oxidation at specific electrical potentials. In-situ impedance measurements were performed during the application of a DC voltage program in a UPW solution containing formic and acetic acids to confirm the efficacy of the techniques discussed herein.

Figure 5:
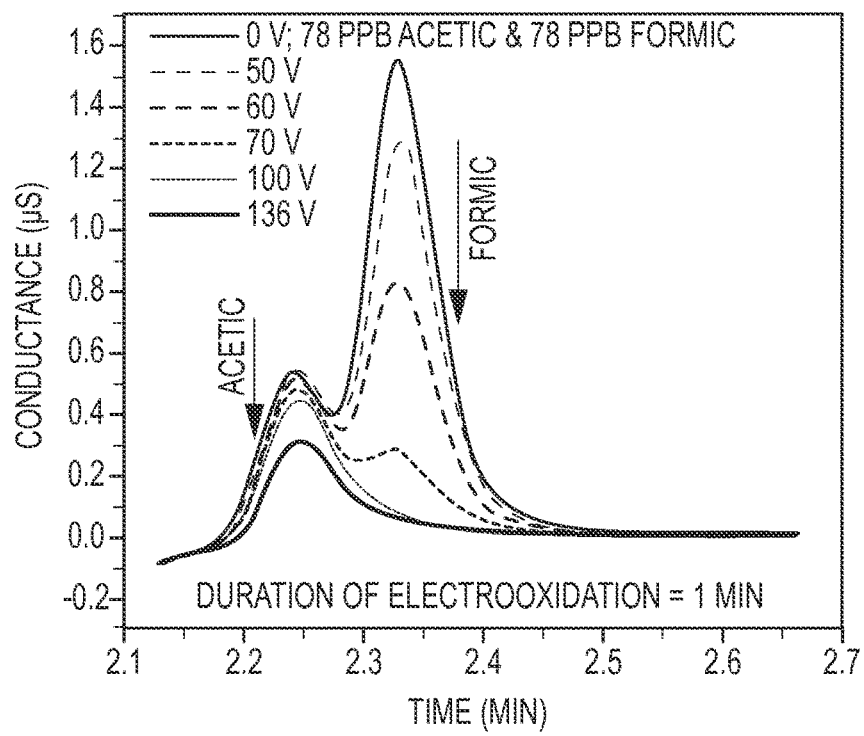
FIG. 5 is a conductance versus time graph illustrating the selective oxidation of formic acid by boron-doped diamond electrodes at various potentials in the presence of acetic acid.

FIG. 5 is a conductance versus time graph illustrating the selective electro-oxidation of formic acid and acetic acid by unmodified BDD electrodes 22 at various potentials in the presence of each other in a solution made using UPW. With reference to FIG. 5, formic acid and acetic acid were present at levels of 78 ppb each, and the electro-oxidation time was 1 minute.

At lower potentials, such as 50 to 70 V, the graph shows significant reduction of the formate concentration with minimal change to the acetate concentration. Above 100 V, the graph shows complete elimination of formic acid from the solution. As the potential is increased, the oxidation of formic acid is enhanced. If the electrical potential or oxidation time is increased further, acetate can also be efficiently electro-catalyzed. The kinetic and thermodynamic selection is may provide the basis of the electrochemical selection.

Figure 6:
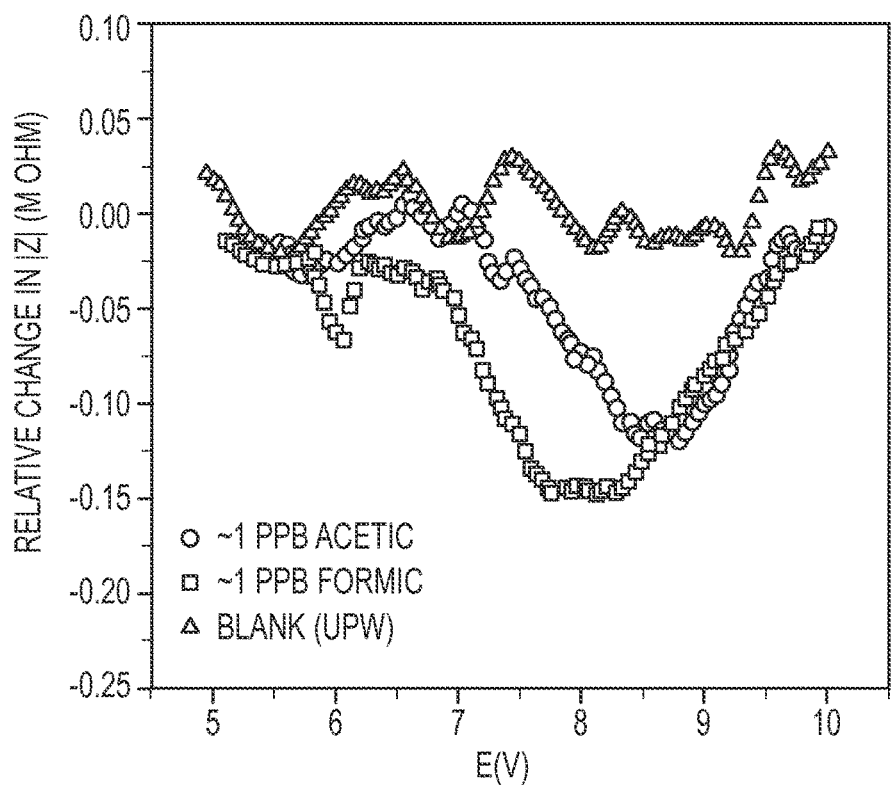
FIG. 6 is a graph showing impedance versus potential profiles for UPW, 1 parts-per-billion (ppb) formic acid, and 1 ppb acetic acid.

FIG. 6 is a graph showing impedance versus potential profiles for UPW, 1 ppb formic acid, and 1 ppb acetic acid. Formic acid is shown in (black) circles, acetic acid is shown in (pink) triangles, and UPW is shown in (red) diamonds as a reference. The onset of a decrease in impedance for a solution containing formic acid started at ~6.8 V and peaked at ~7.8 V with a half wave potential at ~7.3 V. For a solution containing acetic acid, the onset for the decrease in impedance appeared at ~7.2 V and peaked at ~8.6 V with a half wave potential at ~8.0 V. (The impedance peak for the solution containing formic acid was at ~7.8 V, and the impedance peak for the solution containing acetic acid was at ~8.6 V.) FIG. 6 demonstrates the impedance versus potential profiles for C1 and C2 carboxylic acids are unique with speciation being possible between two similar molecules.

The subject matter disclosed in any sentence or paragraph herein can be combined with the subject matter of one or more of any other sentences or paragraphs herein as long as such combinations are not mutually exclusive or inoperable. For example, any of the types of electrochemical cells 20 disclosed may employ any combination of DC and AC voltage programs. Similarly, any of the types of electrochemical cells 20 disclosed may employ any type electrode 22, and moreover, with any combination of DC and AC electrical programs.

Figure 7:
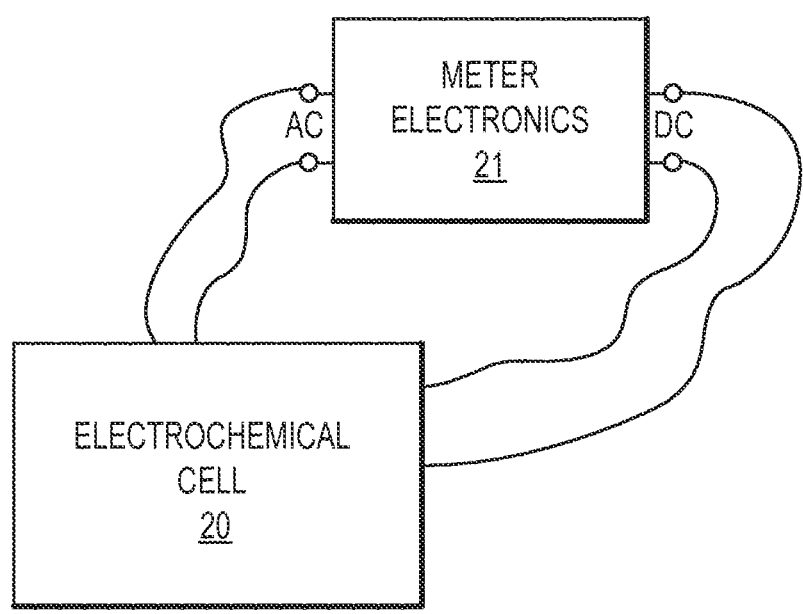
FIG. 7 shows a carbon quantifying system according to the invention.

FIG. 7 shows a carbon quantifying system according to the invention. The carbon quantifying system comprises a carbon quantifying electrochemical cell 20 and meter electronics 21 coupled to the cell 20. The cell 20 can comprise any Of the herein discussed embodiments. The meter electronics 21 provides a means for supplying energy in a programmable manner for inducing an electrical oxidization and/or polarization and/or adsorption of the organic species at the electrodes in the cell 20. The meter electronics 21 also provides a means to measure the resulting electrical signal arising from the electrochemical (oxidation, polarization and/or adsorption) phenomenon occurring in the cell 20. The cell 20 receives a fluid and receives the electrical oxidization program and at least partially oxidizes the fluid. The meter electronics 21 receives an electrical response of the fluid to the electrical oxidization program. The meter electronics 21 is configured to place an electrical oxidization program across electrodes positioned at least partially in the fluid and at least partially oxidizing the carbon materials in the fluid, quantify the carbon materials in the fluid using an electrical response of the fluid to the electrical oxidization program, and detect interfering materials in the fluid using the electrical response.

It will be obvious to those having skill in the art that many changes may be made to the details of the above-described embodiments without departing from the underlying principles of the invention. The scope of the present invention should, therefore, be determined only by the following claims.

The apparatus and method according to the invention can be employed according to any of the embodiments in order to provide several advantages, if desired. The apparatus and method advantageously detects carbon in a fluid. The apparatus and method quantifies carbon or carbon materials in a fluid. The apparatus and method quantifies carbon or carbon materials in a fluid regardless of interfering materials. The apparatus and method identifies any interfering materials in a fluid. The apparatus and method quantifies any interfering materials in a fluid.

The apparatus and method can select for a predetermined carbon material or materials. The apparatus and method is capable of being configured to select for predetermined carbon compounds, including organic carbon compounds. The apparatus and method advantageously can distinguish electrical signals generated from carbon materials from electrical signals generated from interfering materials. The apparatus and method advantageously can distinguish electrical signals generated from carbon materials from electrical signals generated from interfering materials by controlling electrical parameters and electrode characteristics.

The apparatus and method does not require complete oxidization of carbon in a fluid in order to detect and quantify the carbon. The apparatus and method may polarize carbon compounds in a fluid, wherein the polarization can contribute to a quantification process of the carbon. The apparatus and method may polarize organic molecules in a fluid, wherein the polarization can contribute to a quantification of the organic molecules.

The apparatus and method may include a direct current (DC) electrical oxidization that performs one or both of the oxidization of the carbon and polarization of carbon-including compounds, wherein non-oxidized carbon compounds may still be detected and/or measured.

The apparatus and method does not require a membrane that can become clogged, torn, or damaged or that requires calibration.

The apparatus and method enables the detection, quantifying, and/or tracing of sources of contamination of the fluid.

The apparatus and method may include two or more electrodes. The apparatus and method may include four electrodes. The apparatus and method may include electrodes for separately performing operations in the fluid. The apparatus and method may include multiple electrodes for separately performing operations in the fluid. The apparatus and method may include multiple electrodes for separately performing oxidization and polarization operations in the fluid. The apparatus and method may include multiple electrodes for separately performing oxidization and impedance measuring operations in the fluid. The apparatus and method may include multiple electrodes for separately performing oxidization, polarization, and impedance measuring operations in the fluid. The apparatus and method may include four electrodes for separately performing oxidization, polarization, and impedance measuring operations in the fluid.

Unlike in the prior art, complete oxidization of all carbon-including compounds is not necessary. Unlike in the prior art, interfering materials do not need to be eliminated from a fluid. Unlike in the prior art, interfering materials do not need to be separated out beforehand or later screened out of an oxidization and/or polarization result. Unlike in the prior art, interfering materials can also be identified in the fluid. Unlike in the prior art, interfering materials can also be quantified in the fluid.

What is claimed is:

1. A carbon quantifying cell configured to receive a liquid, comprising;
    two or more electrodes positioned at least partially in a liquid; and
    meter electronics including a processor coupled to the two or more electrodes and configured to:
    operate the two or more electrodes and according to a program to at least partially oxidize carbon materials in the liquid,
    apply an AC voltage of a predetermined amplitude across the two or more electrodes during the program,
    receive an electrical response of the liquid to the program, comprising;
    measure a resulting AC current across the two or more electrodes,
    determine a ratio of amplitudes of the measured AC current and the applied AC voltage, and
    determine a phase angle difference between the applied AC voltage and the measured AC current, and
    quantify the carbon materials in the liquid using the electrical response to detect interfering materials in the liquid and using liquid impedance calculated from the measured ratio of amplitudes and the phase angle difference.

2. The carbon quantifying cell of claim 1, wherein the two or more electrodes at least partially comprise a titanium dioxide (TiO2) material.

3. The carbon quantifying cell of claim 1, wherein the two or more electrodes at least partially comprise a boron-doped diamond (BDD) material.

4. The carbon quantifying cell of claim 1, wherein the meter electronics configured to quantify the carbon materials include meter electronics configured to analyze the electrical response in order to determine a speciation of the carbon materials and/or speciation of organic materials in the liquid, wherein the speciation detects a presence of carbon material in the liquid.

5. The carbon quantifying cell of claim 1, wherein the meter electronics configured to quantify the carbon materials include meter electronics configured to determine an identity of the carbon material in the liquid and determine a quantity of the carbon material in the liquid.

6. The carbon quantifying cell of claim 1, wherein the meter electronics configured to quantify the carbon materials include meter electronics configured to determine relative fractions of two or more carbon materials in the liquid.

7. The carbon quantifying cell of claim 1, wherein the program includes one or more of a predetermined DC voltage profile, a predetermined AC voltage profile, or a predetermined current profile.

8. The carbon quantifying cell of claim 1, wherein the meter electronics are configured to apply a varying DC voltage program across the two or more electrodes, thereby preferentially adsorbing and/or oxidizing and/or polarizing a predetermined carbon solute.

* * * * *